United States Patent [19]

Yamashita et al.

[11] Patent Number: 4,784,855

[45] Date of Patent: Nov. 15, 1988

[54] PHARMACEUTICAL COMPOSITIONS AND SUPPOSITORY

[75] Inventors: Chikamasa Yamashita; Kouzo Ishida; Gohachiro Miyamoto; Muneyoshi Ishikawa, all of Tokushima, Japan

[73] Assignee: Otsuka Pharmaceutical Co., Ltd., Tokyo, Japan

[21] Appl. No.: 61,973

[22] Filed: Jun. 15, 1987

[30] Foreign Application Priority Data

Jun. 16, 1986 [JP] Japan .................. 61-141086

[51] Int. Cl.$^4$ .............................................. A61F 9/02
[52] U.S. Cl. .................... 424/436; 424/422; 424/426; 424/423; 424/DIG. 15
[58] Field of Search ............ 424/433, 436, 422, 423, 424/426, DIG. 15

[56] References Cited

U.S. PATENT DOCUMENTS

| | | | |
|---|---|---|---|
| 3,433,791 | 3/1969 | Bentley | 260/285 |
| 3,474,101 | 10/1969 | Bentley | 260/285 |
| 3,931,187 | 1/1976 | Langbein et al. | 546/39 |
| 3,931,189 | 1/1976 | Langbein et al. | 546/39 |
| 4,004,010 | 1/1977 | Langbein et al. | 514/282 |
| 4,699,776 | 10/1987 | Nishihata et al. | 424/436 |

FOREIGN PATENT DOCUMENTS 0171742 7/1985 European Pat. Off.
54-157820 12/1979 Japan .................. 424/436

OTHER PUBLICATIONS

"Preparation of Buprenorphine Suppositories from Commercially Available Injections and Determination of Buprenorphine in the Suppositories", Michiteru Ohtani et al., Yakuzaigaku, vol. 46(3), 229–233 (1986).

Primary Examiner—Thurman K. Page
Attorney, Agent, or Firm—Finnegan, Henderson, Farabow, Garrett & Dunner

[57] ABSTRACT

A pharmaceutical composition for suppository which comprises buprenorphine or its pharmaceutically acceptable acid addition salt as the active ingredient and a mixed base composed of 70 to 95 wt. % of polyethylene glycol with average molecular weight of 200 to 20,000 and 30 to 5 wt. % of propylene glycol.

7 Claims, 1 Drawing Sheet

PHARMACEUTICAL COMPOSITIONS AND SUPPOSITORY

BACKGROUND OF THE INVENTION

This invention relates to a pharmaceutical composition for suppository containing N-cyclopropylmethyl-7α-[(S)-1-hydroxy-1,2,2-trimethylpropyl]-6,14-endo-ethano-6,7,8,14-tetrahydronororipavine (hereinafter referred to as buprenorphine) which is useful as a potent analgesic, or its pharmaceutically acceptable acid addition salt as an active ingredient, having excellent absorption and low irritation.

Buprenorphine is a known compound, and it is, for example, listed on page 207 of The Merck Index (10th Edition), and has been proved by clinical studies to be a potent antagonistic analgesic free from psychotomimetic action which is generally found in narcotic antagonistic analgesics.

Conventionally, buprenorphine is widely used as a parenteral injection for postoperative pain, cancerous pain, anesthesia aid, pain caused by myocardial infraction and others. But the injection is not preferable for patients being treated for a long period, for example, in the cases of intractable chronic pain such as cancerous pain, because frequent administrations are needed, considerable pain accompanies injection, and treatment at home is not possible.

On the other hand, when buprenorphine is orally administered, it is metabolized quickly in the body, and a satisfactory analgesic effect is not expected in its oral dosage form. With this background, the development of buprenorphine suppository has been keenly desired.

However, when buprenorphine is prepared into a suppository form using an oleaginous base which is an ordinary suppository vehicle, the active ingredient cannot be absorbed sufficiently, or when a water-soluble base, (for example, polyethylene glycol) another ordinary suppository vehicle, is used, the absorption rate is low and the rectal mucosa is irritated, and because of these demerits, useful suppositories have not been obtained. Thus, so far, successful intrarectal administration of buprenorphine has not been known.

SUMMARY OF THE INVENTION

It is hence a primary object of this invention to present a suppository composition of buprenorphine which comprises buprenorphine or its salt and a mixed base composed of 70 to 95 wt. % of polyethylene glycol with average molecular weight of 200 to 20,000 and 30 to 5 wt. % of propylene glycol.

This invention, in the light of the above problems, has been achieved by intensive researches of the present inventors into the suppository of buprenorphine, based on the findings that the preparation of buprenorphine blended to a specific vehicle composition hardly irritates or damages the site of application, has a long-duration effect, and shows an excellent absorption rate by intrarectal administration. It is hence an object of this invention to present a novel suppository composition of buprenorphine suited to intrarectal administration.

DETAILED DESCRIPTION OF THE INVENTION

Figure 1:
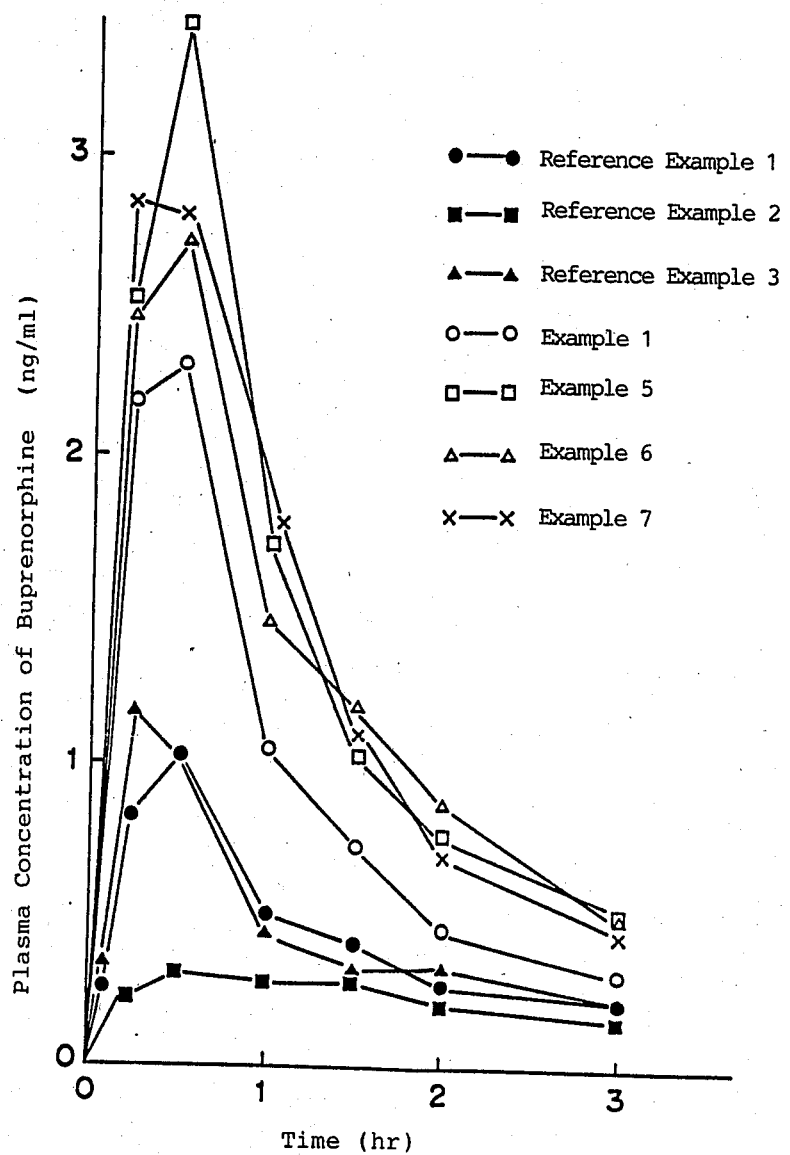
FIG. 1 is a graph showing the results of comparison of absorption of the compositions of this invention and reference compositions in laboratory animals, indicating the relation between the time after administration and the concentration of active ingredient in the blood.

As the polyethylene glycol and propylene glycol used in this invention, any materials customarily used in this field may be used, and for example those listed in the Japanese Pharmacopoeia or the standard of chemical composition of pharmaceuticals outside the Japanese Pharmacopoeia may be preferably employed. As polyethylene glycol, products with average molecular weight of 200 to 20,000, or preferably 400 to 10,000, may be used, and, for example, polyethylene glycol 400, 1,000, 1,500, 1,540, 4,000, and 6,000 are illustrated, which may be used either singly or by mixing two or more kinds.

In the composition of this invention, in order to achieve its objects, polyethylene glycol is present in an amount of from 70 to 95 wt. %, and propylene glycol from 30 to 5 wt. %, or more preferably polyethylene glycol from 85 to 95 wt. % and propylene glycol from 15 to 5 wt. %. With such a blending ratio, an excellent composition with respect to the smooth absorption of active ingredient and reduction of irritation may be obtained.

The blending ratio of buprenorphine or its pharmaceutically acceptable acid addition salt to the mixed base of polyethylene glycol and propylene glycol is not particularly limited, but, to 100 parts by weight of the mixed base, buprenorphine or its pharmaceutically acceptable acid addition salt is usually present in an amount of from 0.001–0.2 part by weight, preferably 0.005–0.16 part by weight, or more preferably 0.01–0.08 part by weight.

In the composition of this invention, any base made only of polyethylene glycol and propylene glycol may be used, but other components may be also added. Examples of other components are usually water, stabilizer, antiseptic, preservative, antioxidant, stiffening agent, forming additive, coloring agent and flavor. Of these additives, the ones customarily used in this field are used and may be added either alone or in combination to the composition of this invention.

As the dosage form used in intrarectal administration of the composition of this invention, anal suppository, soft capsule for intrarectal administration, and ointment form or liquid enema form administered by the use of syringe for intrarectal administration may be used. These dosage forms may be molded by conventional methods.

The preferable dosage form is an anal suppository, and usually in a weight of 0.5 to 3.0 g per piece, and it is preferable to blend in, as the active ingredient, buprenorphine or its pharmaceutically acceptable acid addition salt in an amount of from 0.2 to 0.8 mg. In its usage, one piece should be used once for an adult, and be administered once to three times a day, depending on the condition of the patient.

This invention is further described below by referring to some of the examples to show the method of preparation of the composition of this invention, but it must be understood that this invention is not limited to these examples.

EXAMPLES

EXAMPLE 1

| | |
|---|---|
| Propylene glycol | 10 g |
| Polyethylene glycol 400 | 10 g |
| Polyethylene glycol 1,000 | 30 g |
| Polyethylene glycol 6,000 | 50 g |
| Buprenorphine hydrochloride | 43.2 mg |

After mixing propylene glycol and polyethylene glycol 400, buprenorphine hydrochloride was blended and dissolved, and the mixture was blended with the separately heated and dissolved polyethylene glycol 1,000 and 6,000. The combined mixture was charged into a container for suppository, cooled and solidified, and a suppository of buprenorphine hydrochloride was obtained (suppository weight 1.5 g/piece, each containing 0.6 mg of buprenorphine).

EXAMPLE 2

| | |
|---|---|
| Propylene glycol | 5 g |
| Polyethylene glycol 400 | 15 g |
| Polyethylene glycol 1,000 | 30 g |
| Polyethylene glycol 6,000 | 50 g |
| Buprenorphine hydrochloride | 43.2 mg |

In the same manner as in Example 1, a suppository of buprenorphine hydrochloride was obtained (suppository weight 0.5 g/piece, each containing 0.2 mg of buprenorphine).

EXAMPLE 3

| | |
|---|---|
| Propylene glycol | 15 g |
| Polyethylene glycol 400 | 5 g |
| Polyethylene glycol 1,000 | 30 g |
| Polyethylene glycol 6,000 | 50 g |
| Buprenorphine hydrochloride | 43.2 mg |

In the same manner as in Example 1, a suppository of buprenorphine hydrochloride was obtained (suppository weight 1.5 g/piece, each containing 0.6 mg of buprenorphine).

EXAMPLE 4

| | |
|---|---|
| Propylene glycol | 30 g |
| Polyethylene glycol 1,500 | 10 g |
| Polyethylene glycol 4,000 | 10 g |
| Polyethylene glycol 6,000 | 50 g |
| Buprenorphine hydrochloride | 34.6 mg |

To propylene glycol, buprenorphine hydrochloride was added and dissolved, and the mixture was blended with the separately heated and dissolved polyethylene glycol 1,500, 4,000, and 6,000. The combined mixture was charged into a container for suppository, cooled and solidified, and a suppository of buprenorphine hydrochloride was obtained (suppository weight 2.5 g/piece, each containing 0.8 mg of buprenorphine).

EXAMPLE 5

| | |
|---|---|
| Propylene glycol | 10 g |
| Polyethylene glycol 1,000 | 40 g |
| Polyethylene glycol 4,000 | 20 g |
| Polyethylene glycol 6,000 | 30 g |
| DL-α-tocopherol | 0.5 g |
| Buprenorphine hydrochloride | 43.4 mg |

To propylene glycol, buprenorphine hydrochloride was added and dissolved, and the mixture was blended with the separately heated and dissolved polyethylene glycol 1,000, 4,000, and 6,000, and further DL-α-tocopherol was added thereto. After sufficiently stirring, the mixture was charged into a container for suppository, cooled and solidified, and a suppository of buprenorphine hydrochloride was obtained (suppository weight 1.5 g/piece, each containing 0.6 mg of buprenorphine).

EXAMPLE 6

| | |
|---|---|
| Propylene glycol | 10 g |
| Polyethylene glycol 1,000 | 30 g |
| Polyethylene glycol 6,000 | 50 g |
| Purified water | 10 g |
| Buprenorphine hydrochloride | 43.2 mg |

After mixing propylene glycol and purified water, buprenorphine hydrochloride was added and dissolved, and the mixture was blended with the separately heated and dissolved polyethylene glycol 1,000 and 6,000. The combined mixture was charged into a container for suppository, cooled and solidified, and a suppository of buprenorphine hydrochloride was obtained (suppository weight 1.5 g/piece, each containing 0.6 mg of buprenorphine).

EXAMPLE 7

| | |
|---|---|
| Propylene glycol | 10 g |
| Polyethylene glycol 1,540 | 60 g |
| Polyethylene glycol 4,000 | 30 g |
| Buprenorphine hydrochloride | 43.2 mg |

To propylene glycol, buprenorphine hydrochloride was added and dissolved, and the mixture was blended and stirred with the separately heated and dissolved polyethylene glycol 1,540 and 4,000. The combined mixture was charged into a container for suppository, cooled and solidified, and a suppository of buprenorphine hydrochloride was obtained (suppository weight 1.5 g/piece, each containing 0.6 mg of buprenorphine).

REFERENCE EXAMPLES 1 TO 3

Suppositories in the following compositions were prepared similarly.

REFERENCE EXAMPLE 1

| | |
|---|---|
| Propylene glycol | None |
| Polyethylene glycol 400 | 20 g |
| Polyethylene glycol 1,000 | 30 g |
| Polyethylene glycol 6,000 | 50 g |
| Buprenorphine hydrochloride | 43.2 mg |

REFERENCE EXAMPLE 2

| | |
|---|---|
| Propylene glycol | None |
| Polyethylene glycol 400 | 20 g |
| Polyethylene glycol 1,000 | 30 g |
| Polyethylene glycol 6,000 | 30 g |

-continued

| Witepsol H-15[1] | 20 g |
| Buprenorphine hydrochloride | 43.2 mg |

[NOTE]
[1]Fatty acid triglyceride, tradename Witepsol H-15 ® (manufactured by Dynamit Nobel Co.)

REFERENCE EXAMPLE 3

| Propylene glycol | None |
| Polyethylene glycol 1,000 | 30 g |
| Polyethylene glycol 6,000 | 50 g |
| Purified water | 20 g |
| Buprenorphine hydrochloride | 43.2 mg |

The following experiments were conducted in order to prove the usefulness of the pharmaceutical compositions for suppository of this invention.

Test suppositories (suppository weight 0.1 g/piece, each containing 0.04 mg of buprenorphine) were prepared from the compositions of Examples 1 and 6, and Reference Examples 1, 2 and 3, and a commercial indomethacin suppository (suppository weight 0.1 g/piece) was used as a control. These test preparations were accurately inserted and administered into the rectum of 8 rats each, and the animals were antomized 4 hours after the administration, and the rectum was grossly and histologically observed. And the irritation was compared in the following standard, according to the method proposed by Sato et al. [Yakuzaigaku, Vol. 45, No. 4, P. 298 (1985)]. The results are shown in Table 1.

TABLE 1

Irritation Score
0: normal,   1: extremely slight irritation,
2: slight irritation   3: moderate irritation
4: severe irritation

| Test drug | Gross findings | Histological findings |
|---|---|---|
| Example 1 | 0.2 ± 0.2 | 0.2 ± 0.2 |
| Example 6 | 0.2 ± 0.2 | 0.2 ± 0.2 |
| Reference Example 1 | 0.8 ± 0.2 | 0.8 ± 0.2 |
| Reference Example 2 | 0.6 ± 0.4 | 0.6 ± 0.4 |
| Reference Example 3 | 0.6 ± 0.4 | 1.2 ± 0.6 |
| Indomethacin suppository[1] | 1.2 ± 0.3 | 2.4 ± 0.2 |

NOTE:
[1]commercial product.

As clear from Table 1, the composition of this invention is known to be extremely low in irritation, both grossly and histologically.

Experiment 2 (comparative study on absorption):

Test suppositories (suppository weight 1.5 g/piece, each containing 0.6 mg of buprenorphine) were prepared from the compositions of Examples 1, 5, 6 and 7 and Reference Examples 1, 2 and 3. These test preparations were accurately inserted and administered into the rectum of 5 male NZW rabbits each (weighing 2.3 to 3.5 kg). Blood samples were taken from the auricular vein at 5, 15, 30, 60, 90, 120, and 180 minutes after the administration, and the plasma was obtained by conventional method, and the content of buprenorphine in the plasma was determined by radioimmunoassay, and the absorption was compared.

The results are shown in FIG. 1. As clear from the results, in the composition of this invention, the concentration of buprenorphine, its active ingredient, in the blood was extremely elevated, and an extremely smooth absorption was recognized.

What is claimed is:

1. A suppository composition which comprises N-cyclopropylmethyl-7α-[(S)-1-hydroxy-1,2,2-trimethylpropyl]-6,14endo-ethano-6,7,8,14-tetrahydronororipavine or its pharmaceutically acceptable acid addition salt as the active ingredient and a mixed base consisting essentially of from 70 to 95 wt. % of polyethylene glycol having an average molecular weight of 200 to 20,000 and from 30 to 5 wt. % of propylene glycol.

2. The suppository composition of claim 1, wherein said mixed base contains 85 to 95 wt. % of polyethylene glycol and 15 to 5 wt. % of propylene glycol.

3. The suppository composition of claim 2, wherein the average molecular weight of polyethylene glycol is 400 to 10,000.

4. The suppository composition of claim 3, wherein the content of N-cyclopropylmethyl-7α-[(S)-1-hydroxyl,2,2-trimethypropyl]-6,14-endo-ethano-6,7,8,14-tetrahydronororipavine or its pharmaceutically acceptable acid addition salt is from 0.001–0.2 part by weight per 100 parts by weight of the mixed base.

5. The suppository composition of claim 4 in the dosage form of an anal suppository or a soft capsule for intrarectal administration, or in ointment form or liquid enema form to be administered by means of a syringe for intrarectal administration.

6. The suppository composition of claim 5 in the form of an anal suppository.

7. The suppository composition of claim 5 in the form of a soft capsule for intrarectal administration, or ointment form or liquid enema form to be administered by means of a syringe for intrarectal administration.

* * * * *